United States Patent
Hunt et al.

(10) Patent No.: US 9,714,214 B2
(45) Date of Patent: Jul. 25, 2017

(54) NATURAL OIL DERIVATIVES INCLUDING (METH)ACRYLATE FUNCTIONAL GROUPS

(71) Applicant: Elevance Renewable Sciences, Woodridge, IL (US)

(72) Inventors: Zachary Hunt, Simpsonville, SC (US); S. Alexander Christensen, Northwoods, IL (US)

(73) Assignee: Elevance Renewable Sciences, Inc., Woodridge, IL (US)

(*) Notice: Subject to any disclaimer, the term of this patent is extended or adjusted under 35 U.S.C. 154(b) by 244 days.

(21) Appl. No.: 14/191,927

(22) Filed: Feb. 27, 2014

(65) Prior Publication Data

US 2014/0303336 A1     Oct. 9, 2014

Related U.S. Application Data

(60) Provisional application No. 61/783,269, filed on Mar. 14, 2013.

(51) Int. Cl.
  *C07C 233/17* (2006.01)
  *C07C 233/18* (2006.01)
  (Continued)

(52) U.S. Cl.
  CPC .......... *C07C 233/17* (2013.01); *C07C 233/18* (2013.01); *C07C 233/20* (2013.01); *C07C 237/22* (2013.01); *C08F 220/14* (2013.01)

(58) Field of Classification Search
  CPC ... C07C 233/17; C07C 233/18; C07C 233/20; C07C 237/22; C08F 220/14
  (Continued)

(56) References Cited

U.S. PATENT DOCUMENTS

2007/0243157 A1   10/2007   Tanaka et al.
2008/0108728 A1    5/2008   White et al.
(Continued)

FOREIGN PATENT DOCUMENTS

JP           49-026226        *   3/1974

OTHER PUBLICATIONS

Sigma Aldrich (oleic acid specification sheet, 1 pg, obtained Mar. 30, 2016).*
English language translation of JP 49-026226, Jul. 2012, p. 1-17.*
English translation of Kobayashi, JP-49026226, Mar. 8, 1974, p. 1-17.*

(Continued)

*Primary Examiner* — Jafar Parsa
*Assistant Examiner* — Amy C Bonaparte
(74) *Attorney, Agent, or Firm* — Kilpatrick Townsend & Stockton LLP

(57) ABSTRACT

A compound has Structure I:

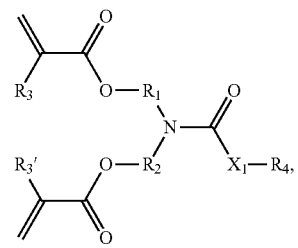

where $R_1$ and $R_2$ independently are $C_2$-$C_{12}$ alkyl groups, $R_3$ and $R_3'$ independently are H or $CH_3$, $X_1$ is a $C_4$-$C_{28}$ alkyl or alkenyl group, and $R_4$ is H or a N,N-bis((meth)acryloylalkyl)-amide group having Structure II:

(Continued)

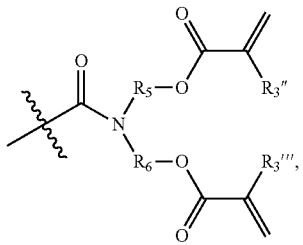

Structure II where $R_5$ and $R_6$ independently are $C_2$-$C_{12}$ alkyl groups, and $R_3''$ and $R_3'''$ independently are either H or $CH_3$.

3 Claims, 5 Drawing Sheets

(51) Int. Cl.
    *C07C 233/20*     (2006.01)
    *C07C 237/22*     (2006.01)
    *C08F 220/14*     (2006.01)

(58) Field of Classification Search
    USPC .............................. 526/304; 554/63; 560/196
    See application file for complete search history.

(56) References Cited

U.S. PATENT DOCUMENTS

2011/0160472 A1    6/2011    Lemke et al.
2012/0010303 A1    1/2012    Mujkic et al.

OTHER PUBLICATIONS

"International Search Report for PCT/US2014/018629", dated May 28, 2014.
Ahamad, et al., "Studies on a Newly Developed Linseed Oil-Based Alumina-Filled Polyesteramide Anticorrosive Coating", 1999, pp. 1679-1687, vol. 72.
Ahmad, et al., "A polyesteramide from Pongamia glabra oil for biologically safe anticorrosive coating", "Progress in Organic Coatings", 2003, pp. 95-102, vol. 47.
Ahmad, et al., "Development of Linseed Oil Based Polyesteramide without Organic Solvent at Lower Temperature", "Journal of Applied Polymer Science", 2007, pp. 1143-1148, vol. 104.
Angewandte Chemie International Edition, 2003, vol. 42, No. 38, Publisher: A Journal of the Gesellschaft Deutscher Chemiker: Angewandte Chemie International Edition, p. 4592-4617.
"Chemical Reviews", Aug. 2009, pp. 3211-3226, vol. 109, No. 8, Publisher: American Chemical Society.
"Chemical Reviews", Jan. 2002, pp. 145-179, vol. 102, No. 1, Publisher: American Chemical Society.
Ng, et al., "Stearic acid coating on magnesium for enhacing corrosion resistance in Hank's solution", 2010, pp. 1823-1830, vol. 204.
Palanisamy, B.S. Rao, "Tetrafunctional Acrylates Based on B-Hydroxy Alkyl Amides as Crosslinkers for UV Curable Coatings", 2006, pp. 297-303, vol. 56, Publisher: Progress in Organic Coatings.
"Pure and Applied Chemistry", 1996, vol. 68, No. 7, Publisher: Official Journal of the International Union of Pure and Applied Chemistry, p. 1591-1595.
Yadav, et al., "Poly (urethane fatty amide)resin from linseed-oil—A renewable resource", "Progress in Organic Coatings", 2009, pp. 27-32, vol. 64.
Zafar, et al., "Ambient-Cured Polyesteramide-Based Anticorrosive Coatings from Linseed Oil—A Sustainable Resource", "Journal of Applied Polymer Science", 2005, pp. 1818-1824, vol. 97.

* cited by examiner

NATURAL OIL DERIVATIVES INCLUDING (METH)ACRYLATE FUNCTIONAL GROUPS

REFERENCE TO RELATED APPLICATIONS

This application claims the benefit of U.S. Provisional Application No. 61/783,269 entitled "Natural Oil Derivatives Including (Meth)acrylate Functional Groups" filed Mar. 14, 2013, which is incorporated by reference in its entirety.

BACKGROUND

Compounds having one or more (meth)acrylate functional groups are used in a wide variety of applications, and particularly in preparing polymers and copolymers. (Meth)acrylate functional groups include both acrylate functional groups having the structure —O—C(=O)—CH=CH$_2$, and methacrylate functional groups having the structure —O—C(=O)—C(CH$_3$)=CH$_2$.

Examples of acrylates include but are not limited to alkyl acrylates such as methyl acrylate, ethyl acrylate, propyl acrylate, butyl acrylate, 2-ethylhexyl acrylate, lauryl acrylate and hexadecyl acrylate; functionalized alkyl acrylates such as hydroxyethyl acrylate, hydroxypropyl acrylate, carboxyethyl acrylate, sulfopropyl acrylate, (2-(acryloyloxy)ethyl)trimethyl ammonium chloride and polyethyleneglycol acrylate. Polyacrylate materials typically are used as coatings and as additives to fluids, lubricants and surface sealants.

Examples of methacrylates include but are not limited to alkyl acrylates such as methyl methacrylate, ethyl methacrylate, propyl methacrylate, butyl methacrylate, 2-ethylhexyl methacrylate, lauryl methacrylate and hexadecyl methacrylate; functionalized alkyl methacrylates such as hydroxyethyl methacrylate, hydroxypropyl methacrylate, carboxyethyl methacrylate, sulfopropyl methacrylate, (2-(methacryloyloxy)ethyl)trimethyl ammonium chloride and polyethyleneglycol methacrylate. Polymethacrylate materials typically are used as rigid plastics and as transparent glazing materials.

Acrylate and methacrylate compounds also are used as comonomers with other types of monomers in preparing copolymers. As acrylate and methacrylate monomers can undergo addition copolymerization with each other and/or with a variety of conventional alkene-functional monomers, the potential applications of (meth)acrylate compounds in polymer chemistry are numerous and diverse.

In addition, compounds having one or more (meth)acrylate functional groups also are used to form dendritic molecules. Dendritic molecules may be used as solubility enhancers, as catalyst supports, as immunoassay components, and as precursors for advanced materials. Species of the poly(amido amine) (PAMAM) class of dendrimers typically are formed by alternating reaction of ethylenediamine and methyl acrylate. Examples of PAMAM dendrimers include but are not limited to [NH$_2$(CH$_2$)$_2$NH$_2$]:(G=0); dendri PAMAM(NH$_2$)$_4$ and its associated higher generation molecules.

The physical and chemical properties of polymers and of dendritic molecules are affected by the chemical structures of the building blocks used to prepare the polymers and/or dendritic molecules. Alteration of the chemical structure, size and/or concentration of these building blocks can allow for modification of the properties of the polymer or dendritic molecule.

It is desirable to expand the chemical structures present in compounds having one or more (meth)acrylate functional groups, so as to expand the useful properties that can be provided by polymers or dendritic molecules formed from the compounds. With regard to polymers, for example, properties such as flexibility, toughness, etc. can be increased by incorporating chemical groups that lower the modulus or that can absorb energy, respectively. This expansion of chemical structures may be accomplished through post-polymerization processing, such as reaction with other reagents or blending with other polymers. It is especially desirable, however, to expand the chemical structures by introducing new chemical structures in the monomeric building blocks from which the polymer is formed. With regard to dendritic molecules, properties such as solubility, chemical reactivity, density, etc. can be changed by incorporating branches having different chain lengths and substitution points.

One potential approach to altering the chemical structure of compounds having one or more (meth)acrylate functional groups is to form the compounds from renewable feedstocks. Renewable feedstocks, such as fatty acids or fatty esters derived from natural oils, have opened new possibilities for the development of a variety of industrially useful substances, including specialty chemicals and intermediates. For example, renewable feedstocks can be used to prepare compounds having combinations of properties that were not available with conventional petroleum feedstocks. In another example, renewable feedstocks can be used to prepare compounds more efficiently, without requiring undesirable reagents or solvents, and/or with decreased amounts of waste or side products.

It would be desirable to provide compounds having one or more (meth)acrylate functional groups that include previously unavailable chemical structures. Preferably such compounds can be used as substitutes for conventional (meth)acrylate-functionalized compounds, while providing an increase in the renewable content of the final product formed using the compounds. Preferably such compounds can provide useful combinations of properties that are difficult to obtain using compounds formed from conventional petroleum feedstocks.

SUMMARY

The scope of the present invention is defined solely by the appended claims, and is not affected to any degree by the statements within this summary.

In one aspect, a compound is provided that has Structure I:

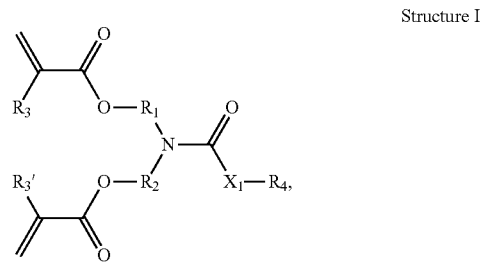

Structure I where R$_1$ and R$_2$ independently are C$_2$-C$_{12}$ alkyl groups, R$_3$ and R$_3$' independently are either H or CH$_3$, X$_1$ is a C$_4$-C$_{28}$ alkyl or alkenyl group, and R$_4$ is selected from the group consisting of H and a N,N-bis((meth)acryloylalkyl)amide group represented by Structure II:

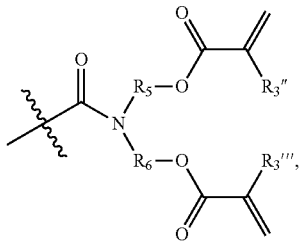

Structure II where $R_5$ and $R_6$ independently are $C_2$-$C_{12}$ alkyl groups, and $R_3''$ and $R_3'''$ independently are either H or $CH_3$.

In another aspect, a ((meth)acryloylalkyl)amide composition is provided that includes the reaction product of a (hydroxyalkyl)amide and a (meth)acryloyl halide, where the (hydroxyalkyl)amide is a reaction product of a metathesized natural oil and a bis(hydroxyalkyl)amine.

In another aspect, a method of making a ((meth)acryloylalkyl)amide composition is provided that includes forming a first reaction mixture including a metathesized natural oil and a bis(hydroxyalkyl)amine, forming a first product mixture including a (hydroxyalkyl)amide formed from the metathesized natural oil and the bis(hydroxyalkyl)amine, forming a second reaction mixture including the (hydroxyalkyl)amide and a (meth)acryloyl halide, and forming a second product mixture including a ((meth)acryloylalkyl) amide.

In another aspect, a method of making a polymer is provided that includes forming a polymerization mixture containing a first monomer containing a compound having Structure I, and forming a product mixture comprising a polymer comprising constitutional units formed from the first monomer.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

Figure 1:
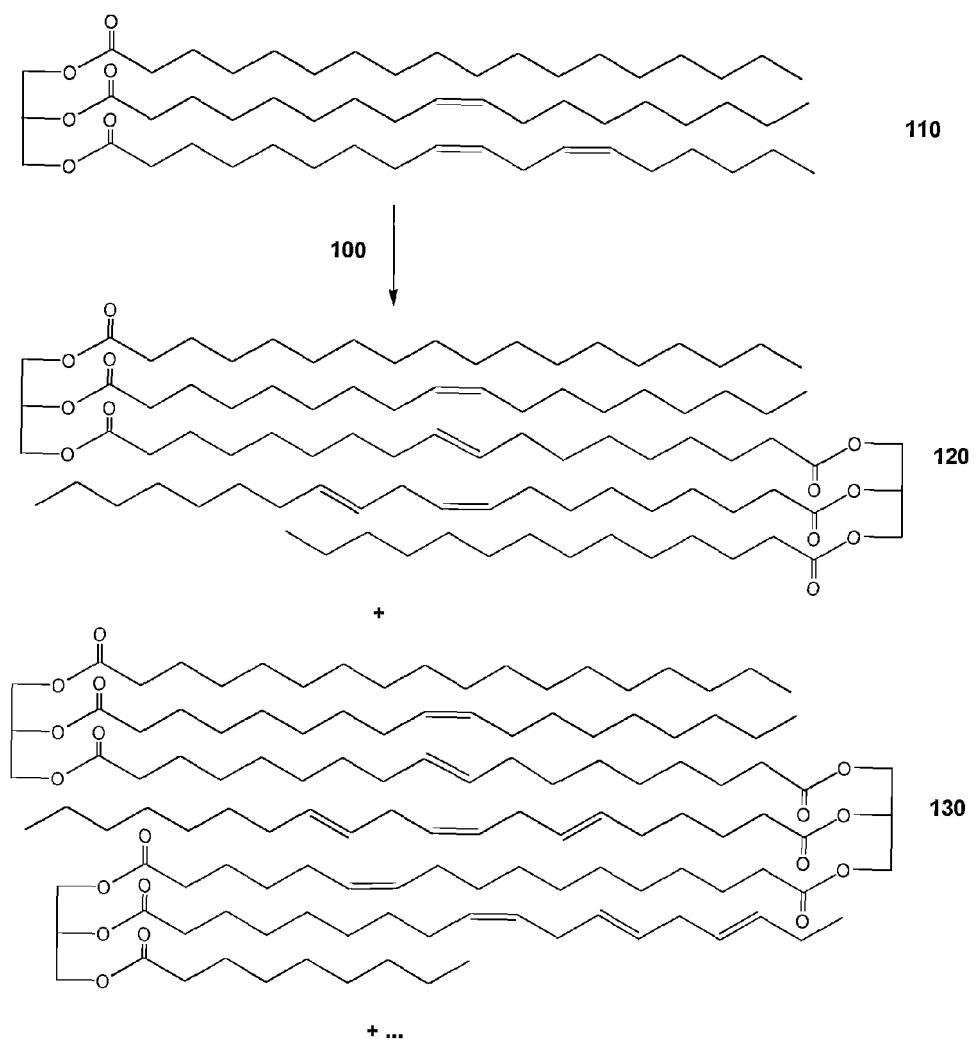
FIG. 1 depicts a reaction scheme for a metathesis reaction of a natural oil.

To provide a clear and more consistent understanding of the specification and claims of this application, the following definitions are provided.

The terms "reaction" and "chemical reaction" refer to the conversion of a substance into a product, irrespective of reagents or mechanisms involved.

The term "reaction product" refers to a substance produced from a chemical reaction of one or more reactant substances.

The term "alkyl group" refers to a group formed by removing a hydrogen from a carbon of an alkane, where an alkane is an acyclic or cyclic compound consisting entirely of hydrogen atoms and saturated carbon atoms.

The term "alkenyl group" refers to a group formed by removing a hydrogen from a carbon of an alkene, where an alkene is an acyclic or cyclic compound consisting entirely of hydrogen atoms and carbon atoms, and including at least one carbon-carbon double bond. A compound containing an alkenyl group is conventionally referred to as an "unsaturated compound".

The term "functional group" refers to a group that includes one or a plurality of atoms other than hydrogen and $sp^3$ carbon atoms. Examples of functional groups include but are not limited to hydroxyl (—OH), protected hydroxyl, ether (—C—O—C—), ketone (>C=O), ester (—C(=O) O—C—), carboxylic acid (—C(=O)OH), cyano (—C≡N), amido (—C(=O)NH—C—), isocyanate (—N=C=O), urethane (—O—C(=O)—NH—), urea (—NH—C(=O)—NH—), protected amino, thiol (—SH), sulfone, sulfoxide, phosphine, phosphite, phosphate, halide (—X), and the like.

The term "(meth)acrylate group" refers to a functional group having the structure —O—C(=O)—CR=CH$_2$), where R is H or $CH_3$. The term "(meth)acrylate group" includes both methacrylate groups (R=$CH_3$) and acrylate groups (R=H).

The terms "(meth)acryloylalkyl" and "(meth)acryloylalkyl group" refer to a functional group formed by removing a hydrogen from an alkyl carbon atom in an organic (meth) acrylate compound (R'—O—C(=O)—CR=CH$_2$), where R' is an alkyl group and R is H or $CH_3$. The term "(meth) acryloyl group" includes both methacryloylalkyl groups (R=$CH_3$) and acryloylalkyl groups (R=H).

The terms "amide", "amide group" and "amido group" refer to a group formed by removing a hydrogen from a carbon atom and/or removing one or both hydrogens from the nitrogen of an organic amide (R—C(=O)—NH$_2$) compound, where R is an organic group. A primary amide group may be represented by the structural formula —C(=O)—NH$_2$, a secondary amide group may be represented by the structural formula —C(=O)—NH—R', and a tertiary amide group may be represented by the structural formula —C(=O)—NR'R", where R' and R" are organic groups.

The term "((meth)acryloylalkyl)amide" refers to a compound that includes a least one alkyl and/or alkenyl group, at least one amide group, and at least one (meth)acryloylalkyl group bonded to the amide nitrogen through a C—N bond.

The term "metathesis catalyst" refers to any catalyst or catalyst system configured to catalyze a metathesis reaction.

The terms "metathesize" and "metathesizing" refer to a chemical reaction involving a single type of olefin or a plurality of different types of olefin, which is conducted in the presence of a metathesis catalyst, and which results in the formation of at least one new olefin product. The phrase "metathesis reaction" encompasses cross-metathesis (a.k.a. co-metathesis), self-metathesis, ring-opening metathesis (ROM), ring-opening metathesis polymerizations (ROMP), ring-closing metathesis (RCM), and acyclic diene metathesis (ADMET), and the like, and combinations thereof.

The terms "natural oils," "natural feedstocks," or "natural oil feedstocks" mean oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include but are not limited to vegetable oils, algal oils, animal fats, tall oils, derivatives of these oils, combinations of any of these oils, and the like. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Tall oils are by-products of wood pulp manufacture. A natural oil may be refined, bleached, and/or deodorized.

The term "natural oil derivatives" refers to compounds or mixtures of compounds derived from one or more natural oils using any one or combination of methods known in the art. Such methods include but are not limited to saponification, transesterification, esterification, hydrogenation (partial or full), isomerization, oxidation, reduction, and the like, and combinations thereof. Examples of natural oil derivatives include but are not limited to gums, phospholipids, soapstock, acidulated soapstock, distillate or distillate sludge, fatty acids and fatty acid alkyl esters such as 2-ethylhexyl ester, hydroxy-substituted variations thereof of the natural oil, and the like, and combinations thereof. For example, the natural oil derivative may be a fatty acid methyl ester (FAME) derived from the glyceride of the natural oil.

The term "metathesized natural oil" refers to the metathesis reaction product of a natural oil in the presence of a metathesis catalyst, where the metathesis product includes a new olefinic compound. A metathesized natural oil may include a reaction product of two triglycerides in a natural feedstock (self-metathesis) in the presence of a metathesis catalyst, where each triglyceride has an unsaturated carbon-carbon double bond, and where the reaction product includes a "natural oil oligomer" having a new mixture of olefins and esters that may include one or more of metathesis monomers, metathesis dimers, metathesis trimers, metathesis tetramers, metathesis pentamers, and higher order metathesis oligomers (e.g., metathesis hexamers). A metathesized natural oil may include a reaction product of a natural oil that includes more than one source of natural oil (e.g., a mixture of soybean oil and palm oil). A metathesized natural oil may include a reaction product of a natural oil that includes a mixture of natural oils and natural oil derivatives. A metathesized natural oil may include a cross-metathesis reaction product of a natural oil with another substance having a carbon-carbon double bond, such as an olefin or ethylene.

The term "polymeric" refers to a substance that includes a polymer.

The term "polymer" refers to a substance having a chemical structure that includes the multiple repetition of constitutional units formed from substances of comparatively low relative molecular mass relative to the molecular mass of the polymer. The term "polymer" includes soluble and/or fusible molecules having chains of repeat units, and also includes insoluble and infusible networks.

The term "monomer" refers to a substance that can undergo a polymerization reaction to contribute constitutional units to the chemical structure of a polymer.

The term "prepolymer" refers to a polymer that can undergo further reaction to contribute constitutional units to the chemical structure of a different polymer. The definitions for "polymer", "monomer" and "prepolymer" are derived from IUPAC, *Pure Appl. Chem.*, Vol. 68, No. 8, pp. 1591-1595, 1996.

Compounds having a plurality of (meth)acrylate functional groups may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical structures. Renewable feedstocks for compounds having a plurality of (meth)acrylate functional groups may include unsaturated compounds having an internal carbon-carbon double bond.

Compounds having a plurality of (meth)acrylate functional groups may be used as monomers in polymerization reactions. The use of a monomer containing a metathesized natural oil derivative can provide additional options for providing polymeric materials having useful combinations of properties, including but not limited to mechanical properties, crosslink density, and post-polymerization reactivity. The compounds having a plurality of (meth)acrylate functional groups also may be used as intermediates for preparing larger compounds through the reaction of one or more of the plurality of (meth)acrylate functional groups with another substance. The use of a monomer and/or an intermediate containing a metathesized natural oil derivative may provide certain advantages over commercial monomers and intermediates, including but not limited to simpler and/or more cost-effective production, reduced variability, improved sourcing, and increased biorenewability.

A compound having a plurality of (meth)acrylate functional groups may be a ((meth)acryloylalkyl)amide represented by Structure I:

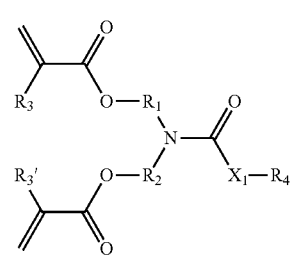

Structure I where $R_1$ and $R_2$ independently are $C_2$-$C_{12}$ alkyl groups, $R_3$ and $R_3'$ independently are either H or $CH_3$, $X_1$ is a $C_4$-$C_{28}$ alkyl or alkenyl group, and $R_4$ is selected from the group consisting of H and a N,N-bis((meth)acryloylalkyl)amide group represented by Structure II:

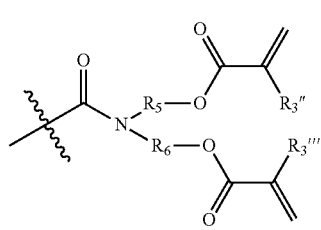

Structure II where $R_5$ and $R_6$ independently are $C_2$-$C_{12}$ alkyl groups, and $R_3''$ and $R_3'''$ independently are either H or $CH_3$.

Preferably $R_1$, $R_2$, $R_5$ and $R_6$ independently are $C_2$-$C_{10}$ alkyl groups, $C_2$-$C_8$ alkyl groups, $C_2$-$C_6$ alkyl groups or $C_2$-$C_4$ alkyl groups. In one example, $R_1$, $R_2$, $R_5$ and $R_6$ are the same, and are a $C_2$-$C_{10}$ alkyl group, a $C_2$-$C_8$ alkyl group, a $C_2$-$C_6$ alkyl group, or a $C_2$-$C_4$ alkyl group.

Preferably $X_1$ is a $C_8$-$C_{22}$ alkyl or alkenyl group, or a $C_{10}$-$C_{16}$ alkyl or alkenyl group. $X_1$ may be derived from a natural oil, and preferably is derived from a metathesized natural oil.

In one example, $R_1$ and $R_2$ are $C_2$ alkyl groups, $R_3$ and $R_3'$ are $CH_3$, and $R_4$ is H. A compound having a plurality of (meth)acrylate functional groups according to this example may be a bis(methacryloylethyl)amide represented by Structure III:

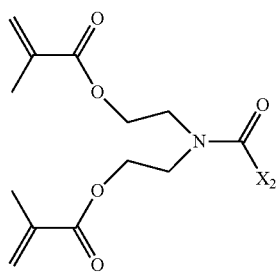

Structure III where $X_2$ is a $C_4$-$C_{28}$ alkyl or alkenyl group. Preferably $X_2$ is a $C_8$-$C_{22}$ alkyl or alkenyl group, or a $C_{10}$-$C_{16}$ alkyl or alkenyl group. $X_2$ may be derived from a natural oil, and preferably is derived from a metathesized natural oil.

In another example, $R_1$ and $R_2$ are $C_2$ alkyl groups, $R_4$ is a bis((meth)acryloylalkyl)amide group represented by Structure (II), $R_5$ and $R_6$ are $C_2$ alkyl groups, and $R_3$, $R_3'$, $R_3''$ and $R_3'''$ are $CH_3$. A compound having a plurality of (meth)acrylate functional groups according to this example may be a tetra(methacryloylethyl)diamide represented by Structure IV:

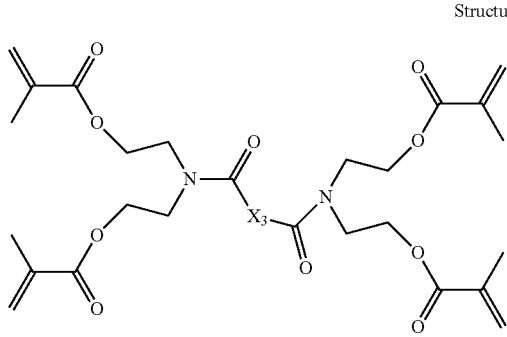

Structure IV where $X_3$ is a $C_4$-$C_{28}$ alkyl or alkenyl group. Preferably $X_3$ is a $C_8$-$C_{22}$ alkyl or alkenyl group, or a $C_{10}$-$C_{16}$ alkyl or alkenyl group. $X_3$ may be derived from a natural oil, and preferably is derived from a metathesized natural oil.

Preferably the compound having a plurality of (meth)acrylate functional groups is derived from a natural oil. More preferably the compound having a plurality of (meth)acrylate functional groups is derived from a metathesized natural oil. Preferably the compound having a plurality of (meth)acrylate functional groups is the reaction product of a (hydroxyalkyl)amide and a (meth)acryloyl halide, where the (hydroxyalkyl)amide is a reaction product of a metathesized natural oil and a bis(hydroxyalkyl)amine. In one example, a metathesized natural oil derivative having a plurality of (meth)acrylate functional groups may be represented by Structure I, III or IV, above.

The metathesized natural oil used to form the compound having a plurality of (meth)acrylate functional groups may be the product of a metathesis reaction of a natural oil in the presence of a metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in paragraphs [0069]-[0155] of US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a transition metal. In some embodiments, the metathesis catalyst includes ruthenium. In some embodiments, the metathesis catalyst includes rhenium. In some embodiments, the metathesis catalyst includes tantalum. In some embodiments, the metathesis catalyst includes nickel. In some embodiments, the metathesis catalyst includes tungsten. In some embodiments, the metathesis catalyst includes molybdenum.

In some embodiments, the metathesis catalyst includes a ruthenium carbene complex and/or an entity derived from such a complex. In some embodiments, the metathesis catalyst includes a material selected from the group consisting of a ruthenium vinylidene complex, a ruthenium alkylidene complex, a ruthenium methylidene complex, a ruthenium benzylidene complex, and combinations thereof, and/or an entity derived from any such complex or combination of such complexes. In some embodiments, the metathesis catalyst includes a ruthenium carbene complex including at least one phosphine ligand and/or an entity derived from such a complex. In some embodiments, the metathesis catalyst includes a ruthenium carbene complex including at least one tricyclohexylphosphine ligand and/or an entity derived from such a complex. In some embodiments, the metathesis catalyst includes a ruthenium carbene complex including at least two tricyclohexylphosphine ligands [e.g., $(PCy_3)_2Cl_2Ru=CH-CH=C(CH_3)_2$, etc.] and/or an entity derived from such a complex. In some embodiments, the metathesis catalyst includes a ruthenium carbene complex including at least one imidazolidine ligand and/or an entity derived from such a complex. In some embodiments, the metathesis catalyst includes a ruthenium carbene complex including an isopropyloxy group attached to a benzene ring and/or an entity derived from such a complex.

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveda-Grubbs-type olefin metathesis catalyst and/or an entity derived therefrom. In some embodiments, the metathesis catalyst includes a second-generation Hoveda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) *Angew. Chem. Int. Ed. Engl.*, 2003, 42, 4592-4633; (b) *Chem. Rev.*, 2002, 102, 145-179; and/or (c) *Chem. Rev.*, 2009, 109, 3211-3226, each of which is incorporated by reference herein in its entirety, except that in the event of any inconsistent disclosure or definition from the present specification, the disclosure or definition herein shall be deemed to prevail.

Metathesis is a catalytic reaction that involves the interchange of alkylidene units among compounds containing one or more double bonds (i.e., olefinic compounds) via the formation and cleavage of the carbon-carbon double bonds. The metathesis reaction of a natural oil containing unsaturated polyol esters can produce oligomers of the unsaturated polyol esters. The resulting oligomers typically contain a mixture of olefins and esters that may include one or more of metathesis monomers, metathesis dimers, metathesis trimers, metathesis tetramers, metathesis pentamers, and higher order metathesis oligomers (e.g., metathesis hexamers, etc.). FIG. 1 depicts chemical structures and reaction schemes related to a metathesis reaction 100 of a natural oil 110, producing metathesis dimer 120, metathesis trimer 130 and higher order metathesis oligomers (not pictured). A metathesis dimer refers to a compound formed when two unsaturated polyol ester molecules are covalently bonded to one another by a metathesis reaction. The molecular weight of the metathesis dimer typically is greater than the molecular weight of the individual unsaturated polyol ester molecules from which the dimer is formed. A metathesis trimer refers to a compound formed when three unsaturated polyol ester molecules are covalently bonded together by metathesis reactions. A metathesis trimer may be formed by the cross-metathesis of a metathesis dimer with an unsaturated polyol ester. A metathesis tetramer refers to a compound formed when four unsaturated polyol ester molecules are covalently bonded together by metathesis reactions. A metathesis tetramer may be formed by the cross-metathesis of a metathesis trimer with an unsaturated polyol ester. Metathesis tetramers may also be formed, for example, by the cross-metathesis of two metathesis dimers. Higher order metathesis oligomers (such as metathesis pentamers, metathesis hexamers, and the like) also may be formed.

The metathesized natural oil may be derived from natural oils such as vegetable oil, algal oil, animal fat, tall oil, derivatives of these oils, or mixtures thereof. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Examples of natural oil derivatives include but are not limited to metathesis oligomers, gums, phospholipids, soapstock, acidulated soapstock, distillate or distillate sludge, fatty acids and fatty acid alkyl ester such as 2-ethylhexyl ester, hydroxyl-substituted variations of the natural oil, and the like, and combinations thereof. For example, the natural oil derivative may be a fatty acid methyl ester (FAME) derived from the glyceride of the natural oil.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

The metathesized natural oil may be a metathesized vegetable oil, a metathesized algal oil, a metathesized animal fat, a metathesized tall oil, a metathesized derivatives of these oils, or a mixture thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Figure 2:
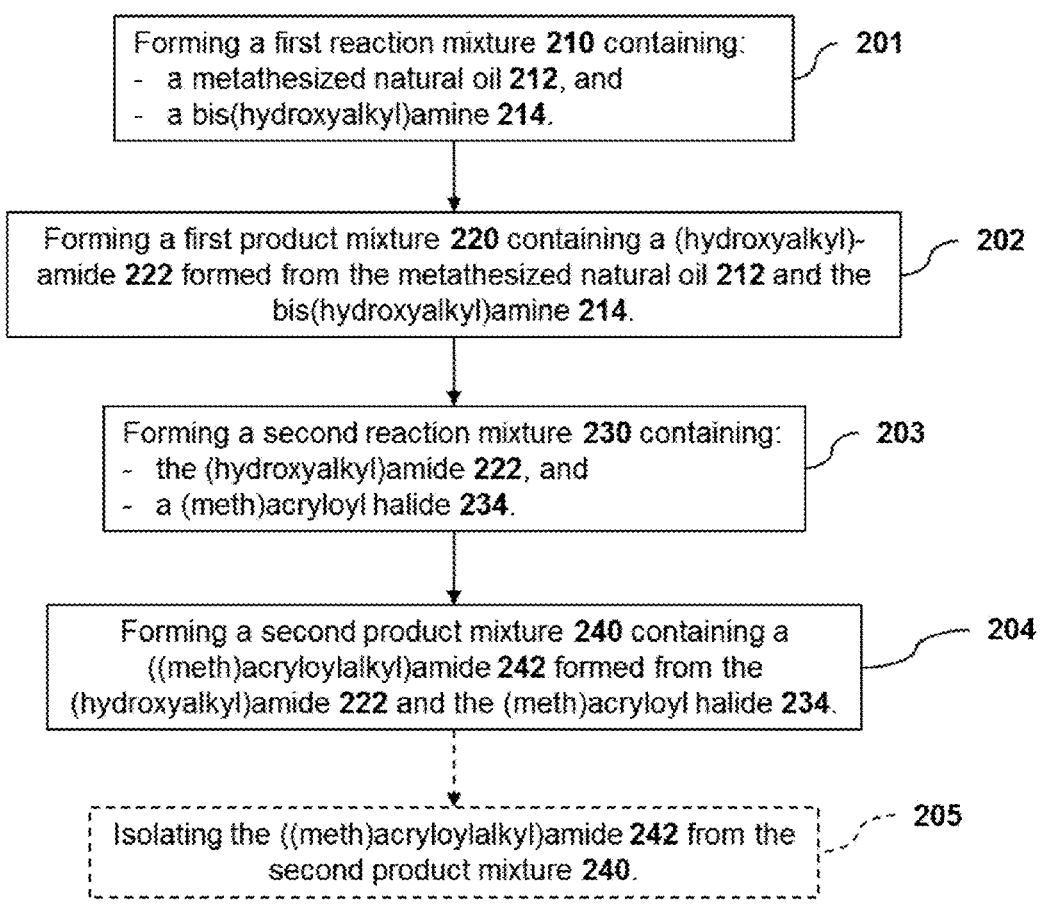
FIG. 2 depicts a method of making a ((meth)acryloylalkyl)amide.

FIG. 2 depicts a method 200 of making a ((meth)acryloylalkyl)amide composition. The method 200 includes forming 201 a first reaction mixture 210 containing a metathesized natural oil 212 and a bis(hydroxyalkyl)amine 214; forming 202 a first product mixture 220 containing a (hydroxyalkyl)amide 222 formed from the metathesized natural oil 212 and the bis(hydroxyalkyl)amine 214; forming 203 a second reaction mixture 230 containing the (hydroxyalkyl)amide 222 and a (meth)acryloyl halide 234; forming 204 a second product mixture 240 containing a ((meth) acryloylalkyl)amide 242 formed from the (hydroxyalkyl) amide 222 and the (meth)acryloyl halide 234; and optionally isolating 205 the ((meth)acryloylalkyl)amide 242 from the second product mixture 240.

The metathesized natural oil 212 in the first reaction mixture 210 may be a metathesized vegetable oil, a metathesized algal oil, a metathesized animal fat, a metathesized tall oil, a metathesized derivatives of these oils, or a mixture thereof, as described above. Preferably the metathesized natural oil 212 includes metathesized soybean oil (MSBO).

The bis(hydroxyalkyl)amine 214 may be a secondary amine that includes two hydroxyalkyl groups bonded to the amine nitrogen through C—N bonds. The bis(hydroxyalkyl) amine 214 may be represented by Structure V:

Structure V where $R_1$ and $R_2$ are as described above regarding Structure I. The two hydroxyalkyl groups (—$R_1$—OH and —$R_2$—OH) may be the same, or they may be different. The hydroxyl group may be at any of a number of positions within the hydroxyalkyl group. Preferably at least one of the hydroxyalkyl groups is a ω-hydroxyalkyl group, in which the hydroxyl group is at the end of the hydroxyalkyl group opposite that of the C—N bond to the secondary amine nitrogen. Examples of bis(hydroxyalkyl)amines include bis (2-hydroxypropyl)amine and N-2-hydroxypropyl-N-hydroxyethylamine. Examples of bis(ω-hydroxyalkyl)amines include but are not limited to diethanolamine. Preferably the bis(hydroxyalkyl)amine 214 includes diethanolamine.

In some embodiments, the amount of bis(hydroxyalkyl) amine present in the first reaction mixture 210 may be between about 0.1 percent by weight (wt %) and about 30 wt % of the metathesized natural oil in the reaction mixture. The amount of bis(hydroxyalkyl)amine in the reaction mixture also may be expressed in terms of the ratio of equivalents of amine in the bis(hydroxyalkyl)amine to ester equivalents in the metathesized natural oil (A:E ratio). For example, in some embodiments, the A:E ratio may be between about 1:100 and about 10:1, or between about 1:10 and about 5:1. In another example, the A:E ratio may be about 1:3, about 2:3, about 1:2, or about 1:1.

The first reaction mixture 210 may include one or more other substances, such as a solvent, a base and/or a catalyst, in addition to the metathesized natural oil 212 and a bis (hydroxyalkyl)amine 214. The metathesized natural oil 212, bis(hydroxyalkyl)amine 214 and optional other substances may be combined simultaneously or in any order.

In one example, the first reaction mixture 210 includes a base to increase the rate of reaction between the bis(hydroxyalkyl)amine and the metathesized natural oil. Examples of bases include but are not limited to sodium carbonate, lithium carbonate, sodium methoxide, potassium hydroxide, sodium hydride, potassium butoxide, potassium carbonate, or mixtures of these. The base may be added to the first reaction mixture 210 neat or as a mixture with a solvent such as water, alcohol, or another organic solvent. In some embodiments, the amount of base in the reaction mixture may be between about 0.1 wt % and about 10 wt % of the metathesized natural oil in the reaction mixture, or between about 1 wt % and about 15 wt % of the metathesized natural oil. In some embodiments, the amount of base in the reaction mixture may be between about 1 wt % and about 10 wt % of the metathesized natural oil, between about 0.1 wt % and about 1.0 wt % of the metathesized natural oil, or between about 0.01 wt % and about 0.1 wt % of the metathesized natural oil.

The forming 202 a first product mixture 220 containing a (hydroxyalkyl)amide 222 may include heating the first reaction mixture 210. In some embodiments, the rate of reaction between the bis(hydroxyalkyl)amine 214 and the metathesized natural oil 212 may be increased by heating the reaction mixture, with or without a base, to at least about 100° C., at least about 120° C., at least about 140° C., at least about 160° C., or between about 100° C. and about 200° C. In some embodiments, the reaction may be carried out at an elevated temperature of between about 30 and about 250° C., between about 80 and about 150° C., or between about 100 and about 125° C. In some embodiments, the reaction mixture may be maintained at the elevated temperature for a time sufficient to form a (hydroxyalkyl)amide 222, such as between about 1 and about 24 hours, or between about 4 and about 24 hours. For example, the reaction mixture may be maintained at the elevated temperature for about 1 hour, about 2 hours, about 4 hours, or about 6 hours. In some embodiments, the reaction may be carried out in an inert atmosphere, such as a nitrogen atmosphere or a noble gas atmosphere. In some embodiments, the reaction may be carried out in an ambient atmosphere.

In some embodiments, heating the first reaction mixture may include maintaining the reaction mixture at a temperature of from about 30° C. to about 150° C. In some embodiments, the reaction mixture temperature may be from about 30° C. to about 100° C., or from about 50° C. to about 85° C. In some embodiments, the reaction mixture may be maintained at a temperature within these ranges for a period of from about 1 hour to about 48 hours, including but not limited to from about 1 hour to about 24 hours, and from about 2 hours to about 8 hours. A (hydroxyalkyl)amide 222 may be formed at a lower temperature and/or within a shorter period of time if the reaction mixture 210 includes a catalyst.

The (hydroxyalkyl)amide 222 may be represented by Structure VI:

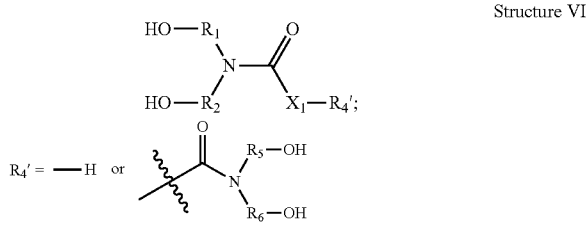

Structure VI where $R_1$, $R_2$, $R_5$, $R_6$ and $X_1$ are as described above regarding Structure I. The (hydroxyalkyl)amide 222 reaction product may have one chemical structure, or the reaction product may be a mixture of compounds having different chemical structures.

The (hydroxyalkyl)amide 222 reaction product optionally may be isolated from the first product mixture 220, such as by removing volatile substances under vacuum. For example, the reaction mixture may be placed under a vacuum for between about 30 minutes and about 1 hour.

Volatile substances may include but are not limited to water, solvent, unreacted bis(hydroxyalkyl)amine, and/or glycerol. For a reaction product that includes a mixture of compounds having different chemical structures, individual compounds may be isolated from the reaction product, or the reaction product may be used as a mixture.

The forming 203 a second reaction mixture 230 includes combining the (hydroxyalkyl)amide 222 and a (meth)acryloyl halide 234. The (meth)acryloyl halide 234 may be methacryloyl chloride, methacryloyl bromide, methacryloyl iodide, acryloyl chloride, acryloyl bromide or acryloyl iodide. The second reaction mixture 230 also may include one or more other substances, such as a solvent and/or a tertiary amine. The (hydroxyalkyl)amide 222, (meth)acryloyl halide 234 and optional tertiary amine and/or solvent may be combined simultaneously or in any order.

In some embodiments, a tertiary amine may be present in the second reaction mixture 230 to remove halide salt reaction products from the reaction mixture, facilitating the progress of the reaction to yield the ((meth)acryloylalkyl) amide product 242. Examples of tertiary amines include but are not limited to trimethylamine, triethylamine, tripropylamine, tributylamine, or mixtures of these. Preferably the molar amount of the tertiary amine is greater than or approximately equal to the molar amount of the (meth) acryloyl halide 234. The tertiary amine may be added to the reaction mixture neat or as a mixture with a solvent such as water, alcohol, or another organic solvent.

In some embodiments, the amount of (meth)acryloyl halide 234 present in the reaction mixture may be between about 50 percent by weight (wt %) and about 100 wt % of the (hydroxyalkyl)amide 222 in the reaction mixture. The amount of (meth)acryloyl halide in the reaction mixture also may be expressed in terms of the ratio of equivalents of halide to hydroxyl equivalents in the (hydroxyalkyl)amide. For example, in some embodiments, the halide:hydroxyl ratio may be between about 1:10 and about 10:1, or between about 1:1 and about 2:1. In another example, the A:E ratio may be about 1:1, about 1.5:1, about 1.75:1, or about 2:1.

The forming 204 a second product mixture 240 containing a ((meth)acryloylalkyl)amide product 242 may include heating the second reaction mixture 230. In some embodiments, the rate of reaction between the (hydroxyalkyl)amide 222 and the (meth)acryloyl halide 234 may be increased by heating the reaction mixture, with or without a tertiary amine to at least about 30° C., at least about 40° C., at least about 50° C., at least about 75° C., or between about 30° C. and about 100° C. In some embodiments, the reaction between the (meth)acryloyl halide 234 and the (hydroxyalkyl)amide 222 may be carried out at an elevated temperature of between about 30 and about 70° C., or between about 30 and about 60° C.

In some embodiments, the second reaction mixture 240 may be maintained, either at room temperature (~25° C.) or at an elevated temperature, for a time sufficient to form a ((meth)acryloylalkyl)amide 222, such as between about 1 and about 24 hours, between about 1 and about 12 hours, or between about 2 hours to about 8 hours. For example, the second reaction mixture may be maintained at the elevated temperature for about 1 hour, about 2 hours, about 4 hours, about 6 hours or about 8 hours. In some embodiments, the reaction between the (meth)acryloyl halide 234 and the (hydroxyalkyl)amide 222 may be carried out in an inert atmosphere, such as a nitrogen atmosphere or a noble gas atmosphere. In some embodiments, the reaction may be carried out in an ambient atmosphere. A ((meth)acryloylalkyl)amide 242 may be formed at a lower temperature and/or within a shorter period of time if the second reaction mixture 230 includes a tertiary amine and/or a catalyst.

The optionally isolating 205 the ((meth)acryloylalkyl) amide 222 from the second product mixture 240 may include removing volatile substances under vacuum. For example, the product mixture may be placed under a vacuum for between about 30 minutes and about 1 hour.

The ((meth)acryloylalkyl)amide 242 reaction product may have one chemical structure, or the reaction product may be a mixture of compounds having different chemical structures. For example, for the ((meth)acryloylalkyl)amide 242 reaction product may include a mixture of compounds represented by Structure I. For a reaction product that includes a mixture of compounds having different chemical structures, individual compounds may be isolated from the reaction product, or the reaction product may be used as a mixture.

Figure 3:
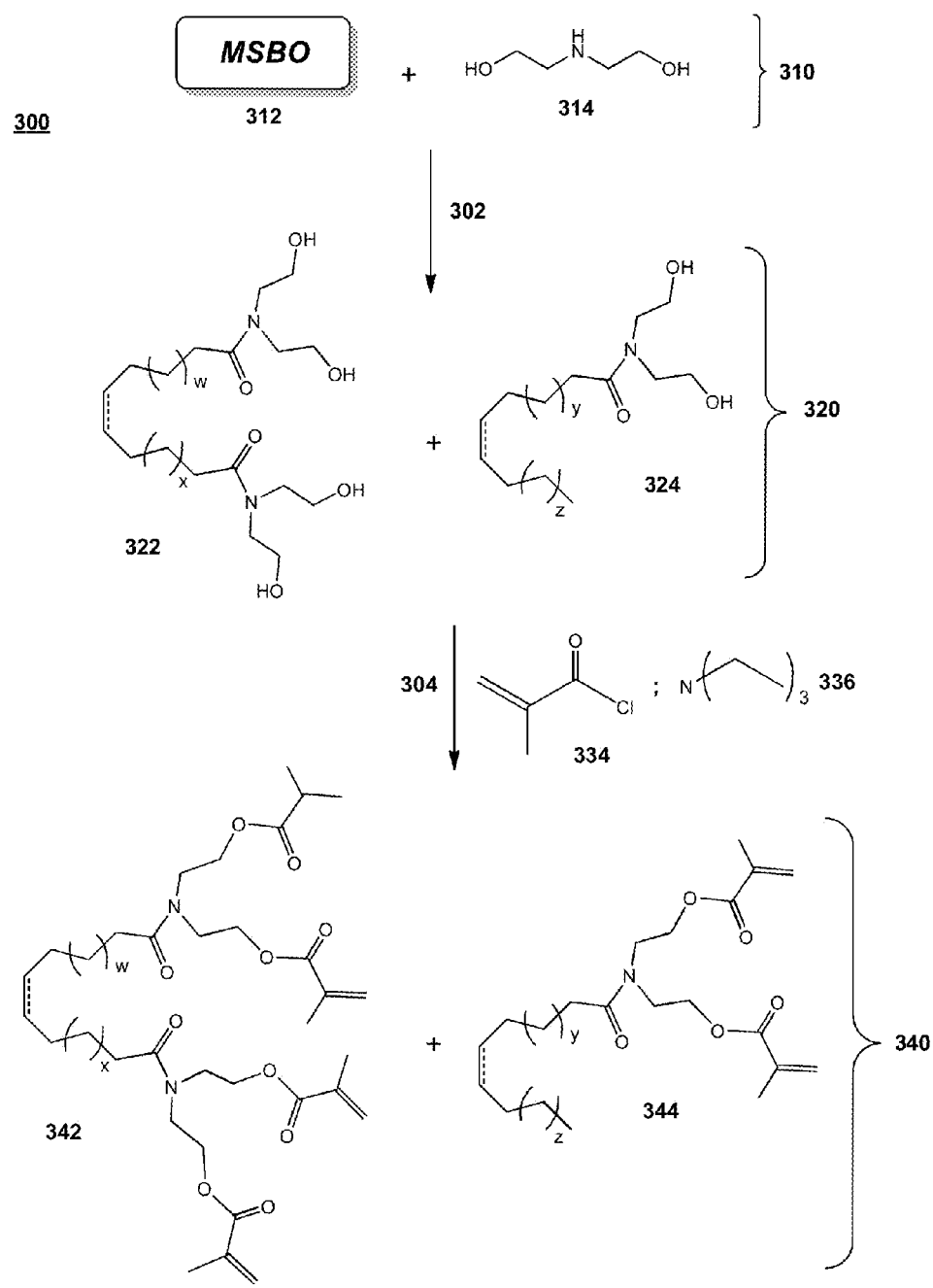
FIG. 3 depicts a representative reaction scheme for a method of forming a ((meth)acryloylalkyl)amide.

FIG. 3 depicts chemical structures and a reaction scheme for an example of a method 300 of making a ((meth) acryloylalkyl)amide composition. The method 300 includes forming a reaction mixture 310 containing metathesized soybean oil (MSBO) 312 as the metathesized natural oil and diethanolamine 314 as the bis(hydroxyalkyl)-amine. The reaction mixture 310 also may include one or more other substances, such as a solvent, a base and/or a catalyst.

Method 300 further includes forming 302 a product mixture 320 containing (hydroxyethyl)amide species, such as 322 and/or 324. In species 322 and 324, w, x, y and z independently are integers from 0 to 18, such that the total number of carbon atoms between the amido groups is from 6 to 28, and the partially dashed double line indicates that species may or may not include one or more carbon-carbon double bonds. The forming 302 may include heating the reaction mixture as described above, including maintaining the reaction mixture at a temperature of from about 30° C. to about 150° C. for a time sufficient to form (hydroxyalkyl) amide species. The tetra(hydroxyethyl)diamide species 322 and bis(hydroxyethyl)amide species 324 are exemplary, as the product mixture 320 may include a number of different species of (hydroxyethyl)amides consistent with Structure VI. Structural variables between the species include but are not limited to the presence and number of carbon-carbon double bonds, the number of carbon atoms in the organic group bonded to the (hydroxyethyl)amide group(s), and branching.

Method 300 further may include isolating a (hydroxyethyl)amide species. As noted above, isolating one or both of the (hydroxyethyl)amide species may include removing volatile substances under vacuum where the volatile substances may include but are not limited to water, solvent, unreacted diethanolamine 314, and/or glycerol. The optional isolating may provide a mixture of (hydroxyethyl)amide species, or it may provide a single (hydroxyethyl)amide species.

Method 300 further includes forming 304 a product mixture 340 containing ((meth)acryloylethyl)amide species, such as 342 and/or 344, where w, x, y and z are as described above with regard to species 322 and 324. The forming 304 may include reacting the (hydroxyethyl)amide species 322 and/or 324 with a (meth)acryloyl halide, such as methacryloyl chloride 334. The forming 304 may include forming a reaction mixture containing the (hydroxyethyl)amide species 322 and/or 324, a methacryloyl halide and optionally a tertiary amine, such as triethylamine 336. The forming 304 occur at room temperature (~25° C.), or it may include heating the reaction mixture as described above, including maintaining the reaction mixture at a temperature of from about 30° C. to about 150° C. for a time sufficient to form (methacryloylethyl)amide species. The tetra(methacryloylethyl)diamide species 342 and bis(methacryloylethyl)amide species 344 are exemplary, as the product mixture 340 may include a number of different species of (methacryloylethyl) amides consistent with Structure I. Structural variables between the species include but are not limited to the presence and number of carbon-carbon double bonds, the number of carbon atoms in the organic group bonded to the (methacryloylethyl)amide group(s), and branching.

Method 300 further may include isolating a ((meth) acryloylethyl)amide species. As noted above, isolating one or both of the ((meth)acryloylethyl)amide species may include removing volatile substances under vacuum. The optional isolating may provide a mixture of ((meth)acryloylethyl)amide species, or it may provide a single ((meth) acryloylethyl)amide species.

A compound having a plurality of (meth)acrylate functional groups may be used in a polymerization reaction. Compounds having an acrylate or a methacrylate functional group may undergo addition polymerization reactions. Compounds having an acrylate or a methacrylate functional group also may undergo addition copolymerization reactions with other compounds having terminal alkenyl groups. Monomers having a plurality of (meth)acrylate functional groups may be used as chain extenders, as crosslinkers, or as branching points in a polymer.

Figure 4:
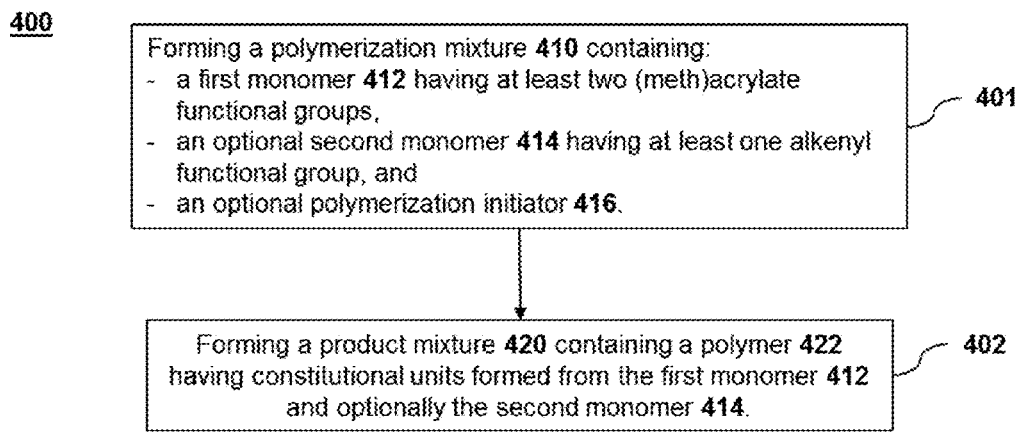
FIG. 4 depicts a method of making a polymer.

FIG. 4 represents a method 400 of forming a polymer. The method 400 includes forming 401 a polymerization mixture 410 containing a first monomer 412 having at least two (meth)acrylate functional groups, an optional second monomer 414 having at least one alkenyl functional group, and an optional polymerization initiator 416. The method further includes forming 402 a product mixture 420 containing a polymer 422 having constitutional units formed from the first monomer 412 and optionally the second monomer 414.

The first monomer 412 having at least two (meth)acrylate functional groups may be a compound having a plurality of (meth)acrylate functional groups as described above. The first monomer may be represented by one or more of Structures I, III and IV. The first monomer may be a reaction product of a (hydroxyalkyl)amide and a (meth)acryloyl halide, where the (hydroxyalkyl)amide is a reaction product of a metathesized natural oil and a bis(hydroxyalkyl)amine.

The optional second monomer 414 may include any polymerizable substance that contains an alkenyl group. Examples of such unsaturated polymerizable substances include ethylene; styrenes such as styrene and methyl styrene; halogenated vinyl compounds such as vinyl chloride, vinylidene chloride and tetrafluoroethylene; acrylates; acrylamide; acrylonitrile; N-vinyl pyrrolidone; and substituted derivatives thereof. Examples of acrylate monomers include butyl acrylate, 2-ethylhexyl acrylate, ethyl acrylate, lauryl acrylate, hexadecyl acrylate, and methacrylate derivatives of these monomers. Examples of acrylamide monomers include acrylamide, N,N-dimethyl acrylamide, N-ethyl acrylamide, N-isopropyl acrylamide and hydroxymethyl acrylamide, and methacrylamide derivatives of these monomers.

The optional polymerization initiator 416 may include a free radical polymerization initiator, a cationic polymerization initiator, or an anionic polymerization initiator. A polymerization initiator is not required in the reaction mixture 410, however, as addition polymerization may be initiated by heat or by electromagnetic radiation such as visible or ultraviolet light.

The polymerization mixture 410 may include only the monomer(s) and optionally an initiator, or it may include one or more other substances, such as a solvent, a buffer or a salt. Examples of solvents include but are not limited to protic solvents such as water, methanol, ethanol, isopropyl alcohol (IPA) and butanol; and aprotic solvents such as tetrahydrofuran (THF), dioxane, dimethyl formamide (DMF), toluene and xylene.

Preferably forming 401 the polymerization mixture 410 includes combining the monomers with a free radical addition polymerization initiator. Selection of a particular free radical polymerization initiator may depend on a number of factors including but not limited to the polymerization temperature, the type of comonomers, and whether a solvent is present in the reaction mixture. Examples of free radical polymerization initiators include but are not limited to peroxides such as hydrogen peroxide; alkyl peroxides such as di-t-butyl peroxide, di-t-amyl peroxide, dilauroyl peroxide and 2,5-bis(t-butylperoxy)-2,5-dimethylhexane; acyl peroxides; aryl peroxides such as benzoyl peroxide, dicumyl peroxide and t-butyl peroxybenzoate; and hydroperoxides such as t-butyl hydroperoxide. Examples of free radical polymerization initiators include but are not limited to azo compounds such as 2,2'-azobisisobutyro-nitrile (AIBN), 2,2'-azobis(2-methylbutyronitrile), 2,2'-azobis(2,4-dimethylvaleronitrile), 2,2'-azobis(2-amidino-propane)-dihydrochloride, and 2,2'-azobis(N,N'-dimethylene-isobutylamidine). Examples of free radical polymerization initiators include but are not limited to persulfates such as potassium persulfate and ammonium persulfate. The amount of polymerization initiator may range, for example, from about 0.01 to 5 mol % based on the total moles of comonomers present.

Forming 402 a product mixture 420 containing a polymer 422 having constitutional units formed from the first monomer 412 and optionally the second monomer 414 may include heating the polymerization mixture. The polymerization mixture may be heated to a temperature of at least about 30° C., including but not limited to a temperature from about 30° C. to about 250° C., from about 40° C. to about 200° C., from about 50° C. to about 175° C., or from about 60° C. to about 160° C. The polymerization mixture may be heated for at least about 1 hour, including but not limited to from about 1 hour to about 100 hours, from about 5 hours to about 50 hours, from about 10 hours to about 30 hours, or from about 15 hours to about 25 hours.

Forming 402 a product mixture 420 may include isolating the polymer 422. Isolating the polymer 422 may include removing volatile starting material and/or byproducts under reduced pressure and/or heat. Isolating the polymer 422 may include dissolving the polymer in a solvent to form a solution, and precipitating the polymer by contacting the solution with a non-solvent for the polymer. Isolating the polymer 422 may include dissolving the polymer in a solvent to form a solution, and removing low molecular weight species from the solution by dialysis against the solvent.

Figure 5:
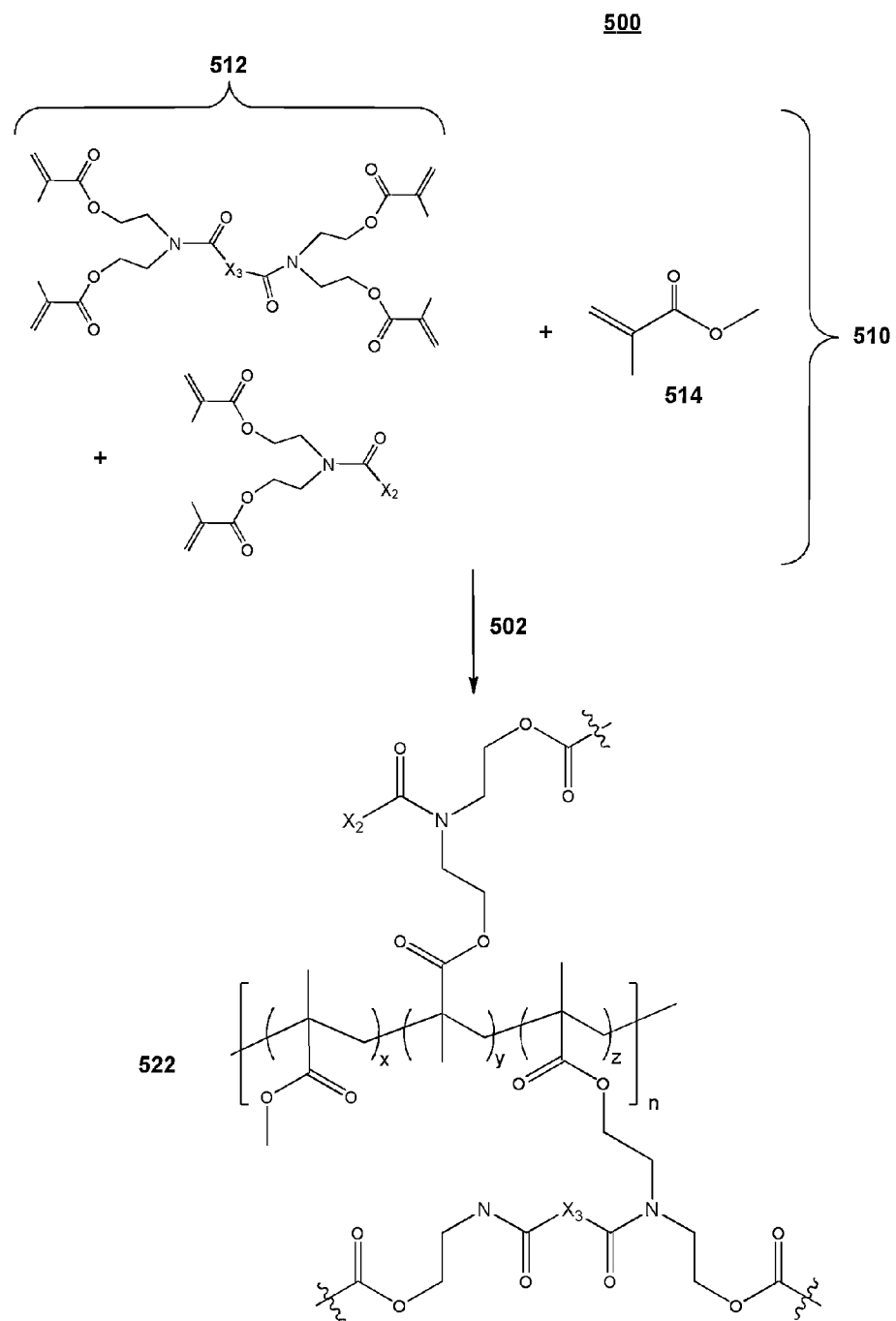
FIG. 5 depicts a representative reaction scheme for a method of forming a copolymer.

FIG. 5 depicts chemical structures and a reaction scheme for an example of a method 500 of forming a copolymer. Method 500 includes forming a reaction mixture 510 containing first monomers 512 having at least two methacrylate functional groups and a second monomer 514 having at least one alkenyl functional group, and forming 502 a product mixture 520 containing a copolymer 522 having constitutional units formed from the first monomers 512 and the second monomer 514.

In the first monomers 512 and in the copolymer 522, $X_2$ and $X_3$ are as described above for Structures III and IV. The second monomer 514 depicted in FIG. 5 is methyl methacrylate. In the copolymer 522, x+y+z=1, and n may be from 2 to 100, from 3 to 50, or from 4 to 25. The "⁓" symbol represents a potential linkage to another polymer chain.

A compound having a plurality of (meth)acrylate functional groups, such as the reaction product of a metathesized natural oil and a bis(aminoalkyl) amine and/or a compound represented by Structure I above, may be used to form a dendritic molecule. In one example, the compound having a plurality of (meth)acrylate functional groups may be used as a substitute for some or all of the methyl acrylate typically used in the synthesis of PAMAM dendrimers. In another example, the compound having a plurality of (meth)acrylate functional groups may be used as the core in the divergent synthesis of a dendrimer. Reaction of the compound with ethylenediamine, followed by reaction with methyl acrylate, may provide a dendrimer analogous to the PAMAM system, but with a core that is more flexible and less sterically hindered.

The following examples and representative procedures illustrate features in accordance with the present teachings, and are provided solely by way of illustration. They are not intended to limit the scope of the appended claims or their equivalents, and numerous variations can be made to the following examples that lie within the scope of these claims.

EXAMPLES

Example 1

Formation of (Hydroxyalkyl)Amide Compounds

Compounds having at least two hydroxyl functional groups were formed by reacting a metathesized natural oil and a bis(hydroxyalkyl)amine. Diethanolamine (150 grams (g)) and potassium t-butoxide (3.5 g) were combined in a flask equipped with a condenser, and the mixture was heated to 115° C. and stirred. To this mixture, metathesized soybean oil (MSBO; 400 g) was added dropwise. Table 1 lists the reactants present in the reaction mixture.

TABLE 1

Reactants used to form compound having at least two hydroxyl groups

|  | MSBO | Diethanolamine | potassium t-butoxide |
|---|---|---|---|
| molecular weight | 200* | 105.14 g/mol | 112.21 g/mol |
| mass | 400 g | 150 g | 3.5 g |
| moles | 1.426 | 1.427 | 0.312 |
| equivalents | 1 | 1 | 0.022 |

*saponification value

The mixture was maintained at 115° C. for 1.5 hours after the MSBO addition was complete. The mixture was allowed to cool, and was then dissolved in diethyl ether, washed with a saturated sodium chloride solution, and dried. The ether was removed from the product by rotary evaporation to provide a mixture of monomers having at least two hydroxyl functional groups and containing a group derived from the MSBO.

Characterization of the product by Fourier Transform Infrared Spectroscopy (FTIR) was consistent with full conversion of the ester groups in the MSBO to N,N-diethanolamide groups. The hydroxyl value (OHV) was determined to be 285, which corresponds to 5.079 millimoles of hydroxyl groups per gram. While neither desiring to be bound by any particular theory nor intending to limit in any measure the scope of the appended claims or their equivalents, it is presently believed that the product may be represented by Structure VII:

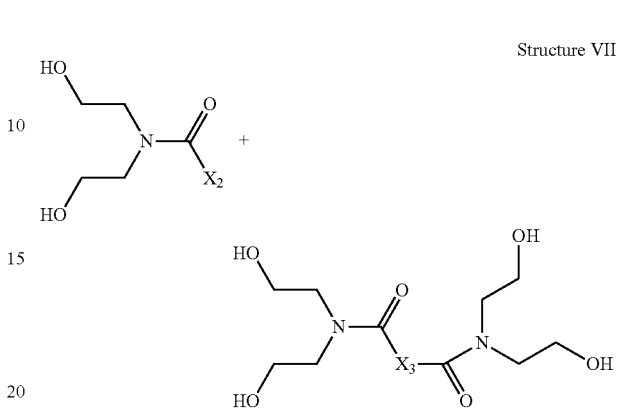

Structure VII where $X_2$ and $X_3$ are as described above with regard to Structures III and IV.

Example 2

Formation of ((Meth)Acryloylalkyl)Amide Compounds

Compounds having at least two (meth)acrylate functional groups were formed by reacting the (hydroxyalkyl)amide compounds of Example 1 and a (meth)acryloyl halide. In a flask containing dichloromethane, 30 g of the product of Example 1 was dissolved. Methacryloyl chloride (19.87 g) and triethylamine (19.24 g) were added to this solution, and the mixture was stirred for approximately 12 hours at room temperature (~25° C.). Table 2 lists the reactants present in the reaction mixture.

TABLE 2

Reactants used to form compound having at least two methacrylate groups

|  | (Hydroxyalkyl)amides | Methacryloyl chloride | Triethylamine |
|---|---|---|---|
| molecular weight | 285* | 104.54 g/mol | 101.10 g/mol |
| mass | 30 g | 19.87 g | 19.24 g |
| moles | 0.1524 | 0.1905 | 0.1905 |
| equivalents | 1 | 1.25 | 1.25 |

*hydroxyl value (OHV)

The mixture was washed with a saturated sodium chloride solution, and the organic layer was dried over sodium sulfate. The dichloromethane solvent was removed from the product by rotary evaporation, and the product was washed in methanol. The resulting product (33.8 g) was an amber liquid.

Characterization of the product by Fourier Transform Infrared Spectroscopy (FTIR) was consistent with full conversion of the hydroxyl groups in the (hydroxyalkyl)amide compounds to methacryloyl groups. While neither desiring to be bound by any particular theory nor intending to limit in any measure the scope of the appended claims or their equivalents, it is presently believed that the product may be represented by Structures III and IV, where the $X_2$ and $X_3$ groups are alkyl groups or alkenyl groups from the MSBO.

The ability of the methacrylate functional groups in the reaction product to polymerize was confirmed by storing the product in a clear glass jar at room temperature, without protecting the product from ambient light sources. After 60 hours, the product had transformed from a liquid to a solid, which was insoluble.

Example 3

Formation of Poly(Methyl Methacrylate) and of Copolymers Containing Methyl Methacrylate Units and ((Meth)Acryloylalkyl)Amide Units A polymer was formed by polymerizing a first monomer having at least one (meth)acrylate group, and copolymers were formed by copolymerizing the first monomer and a second monomer having at least two (meth)acrylate groups, where the second monomer is a derivative of a metathesized natural oil. Methyl methacrylate was polymerized by free radical polymerization to form poly(methyl methacrylate), and was copolymerized with the ((meth)acryloylalkyl)amide compounds of Example 2. The polymerization/copolymerization reactions were carried out by forming polymerization mixtures containing tetrahydrofuran solvent (THF), methyl methacrylate (MMA), azoisobutyronitrile initiator (AIBN) and optionally a portion of the reaction product of Example 2. Table 3 lists the amounts of methacrylate and (methacryloylalkyl)amide present in the polymerization mixtures. Each polymerization mixture also included 4.446 g THF solvent and 0.14 g AIBN initiator (0.3 wt % of MMA). The percent of (methacryloylalkyl)amide listed is the weight percent with regard to the total mass of methacrylate-functionalized monomers.

TABLE 3

| Methacrylate-functionalized monomers used to form polymers and copolymers | | | |
| --- | --- | --- | --- |
| | Methyl methacrylate | (Methacryloylalkyl)amide | |
| | (g) | (g) | (percent*) |
| A | 4.7 g | — | 0 wt % |
| B | 4.7 g | 11.7 mg | 0.25 wt % |
| C | 4.7 g | 23.5 mg | 0.50 wt % |
| D | 4.7 g | 47 mg | 1.0 wt % |

The polymerization mixtures were placed in vials, sparged with nitrogen and/or argon gas for 15 seconds, and then sealed and heated at 60° C. for 8 hours. The resulting product was dissolved in dichloromethane, and the polymer was precipitated by pouring the liquid into methanol.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent and that such new combinations are to be understood as forming a part of the present specification.

What is claimed is:

1. A compound having Structure I:

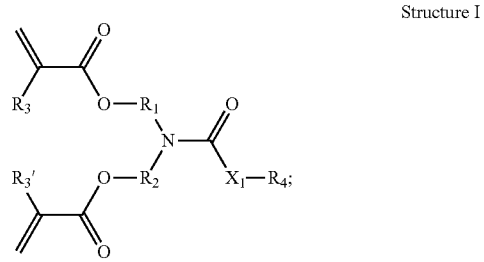

Structure I wherein $R_1$ and $R_2$ independently are $C_2$-$C_{12}$ alkyl groups, $R_3$ and $R_3'$ independently are H or $CH_3$, $X_1$ is a $C_{10}$-$C_{16}$ alkenyl group, and $R_4$ is a N,N-bis((meth)acryloylalkyl)-amide group having Structure II:

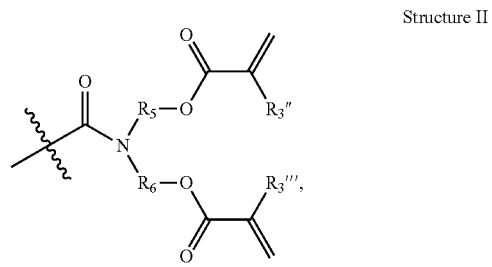

Structure II wherein $R_5$ and $R_6$ independently are $C_2$-$C_{12}$ alkyl groups, and $R_3''$ and $R_3'''$ independently are either H or $CH_3$.

2. The compound of claim 1, wherein $R_1$, $R_2$, $R_5$ and $R_6$ independently are $C_2$-$C_6$ alkyl groups.

3. A compound having Structure IV:

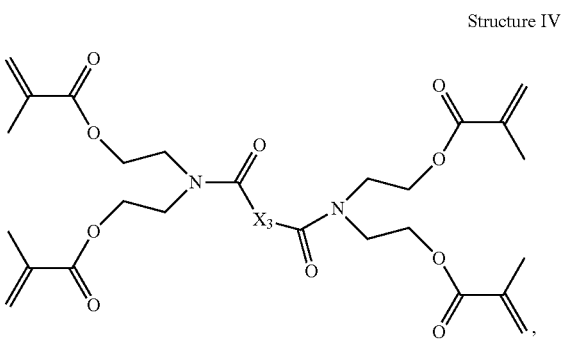

Structure IV wherein $X_3$ is a $C_{10}$-$C_{16}$ alkenyl group.

* * * * *